United States Patent
Sahler et al.

(10) Patent No.: US 10,709,325 B2
(45) Date of Patent: Jul. 14, 2020

(54) MONITORING COMPONENT AND METHOD FOR MONITORING A VISUAL CAPACITY MODIFICATION PARAMETER OF A USER OF AT LEAST ONE DISPLAY DEVICE

(71) Applicant: Essilor International, Charenton-le-pont (FR)

(72) Inventors: Jean Sahler, Charenton-le-Pont (FR); Marie Lore, Charenton-le-Pont (FR); Paul Gil, Charenton-le-Pont (FR); Guillaume Broutin, Charenton-le-Pont (FR); Nisha Singh, Singapore (SG); Konogan Baranton, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 21 days.

(21) Appl. No.: 15/741,008

(22) PCT Filed: Jun. 30, 2016

(86) PCT No.: PCT/EP2016/065348
§ 371 (c)(1),
(2) Date: Dec. 29, 2017

(87) PCT Pub. No.: WO2017/001584
PCT Pub. Date: Jan. 5, 2017

(65) Prior Publication Data
US 2018/0184893 A1      Jul. 5, 2018

(30) Foreign Application Priority Data

Jul. 1, 2015 (EP) .................... 15306072

(51) Int. Cl.
*A61B 3/10* (2006.01)
*A61B 3/00* (2006.01)
(Continued)

(52) U.S. Cl.
CPC .............. *A61B 3/10* (2013.01); *A61B 3/0025* (2013.01); *A61B 3/032* (2013.01);
(Continued)

(58) Field of Classification Search
CPC ................................ A61B 3/10; A61B 3/0025
See application file for complete search history.

(56) References Cited

U.S. PATENT DOCUMENTS

| | | |
|---|---|---|
| 2014/0111558 A1 | 4/2014 | Ishitani et al. |
| 2014/0285436 A1 | 9/2014 | Wu |
| 2015/0055087 A1 | 2/2015 | Wu |

FOREIGN PATENT DOCUMENTS

JP      8-286646 A      11/1996

OTHER PUBLICATIONS

International Search Report and Written Opinion dated Aug. 31, 2016 in PCT/EP2016/065348 filed Jun. 30, 2016.

*Primary Examiner* — Jack Dinh
(74) *Attorney, Agent, or Firm* — Oblon, McClelland, Maier & Neustadt, L.L.P.

(57) ABSTRACT

A method for monitoring a visual capacity modification parameter of a user of at least one display device, the visual capacity modification parameter being indicative of the modification of a parameter linked to the visual capacity of the user related to the use of the at least one display device, the method includes a display use data determining step during which display use data indicative of a use of the at least one display device by the user are determined, a visual capacity modification parameter determining step during which a modification parameter of the visual capacity of the user is determined based on said display use data, and an information generating step during which an information based on said modification parameter of the visual capacity of the user is generated.

13 Claims, 1 Drawing Sheet

(51) Int. Cl.
*G09G 3/36* (2006.01)
*G02B 27/00* (2006.01)
*A61B 3/032* (2006.01)
*G02B 27/01* (2006.01)
*A61B 5/00* (2006.01)

(52) U.S. Cl.
CPC ....... *G02B 27/0093* (2013.01); *G02B 27/017* (2013.01); *G09G 3/3611* (2013.01); *A61B 5/0022* (2013.01); *A61B 2560/028* (2013.01); *A61B 2560/0266* (2013.01); *A61B 2560/0271* (2013.01); *G02B 2027/014* (2013.01); *G02B 2027/0181* (2013.01); *G09G 2354/00* (2013.01); *G09G 2370/022* (2013.01)

MONITORING COMPONENT AND METHOD FOR MONITORING A VISUAL CAPACITY MODIFICATION PARAMETER OF A USER OF AT LEAST ONE DISPLAY DEVICE

FIELD OF THE INVENTION

The invention relates to a method and a monitoring component for monitoring a visual capacity modification parameter of a user of at least one display device, the visual capacity modification parameter being indicative of the modification of a parameter linked to the visual capacity of the user related to the use of the at least one display device The invention further relates to a display device or, a head mounted device configured to be worn by a wearer, comprising a display configured to be watched by the wearer, at least one sensor configured to sense display use data indicative of a use of the at least one display device by the wearer, and a communication component configured to communicate display use data indicative of a use of the at least one display device by the wearer sensed by the at least one sensor to a monitoring component.

BACKGROUND OF THE INVENTION

Some studies shows that people spend more and more time watching screen displays, for example TV, computer screen, laptop, smartphone, tablet, and tomorrow augmented reality eyewear display, watch, etc.

Such screens require a lot of our near and/or intermediate vision, which can lead to vision performance loss, in short or long term, temporarily or permanently.

Furthermore these screens emit cold and aggressive light for the eyes.

Symptoms could appear, usually at the end of the day: for example blurred vision, eye dryness, headaches, mood, diplopia, strabismus, as well as an increase in myopia over the long term.

Therefore, there is a need to provide a method for monitoring a parameter linked to the visual capacity of the user related to the use of display devices.

An aim of the present invention is to propose such solution.

SUMMARY OF THE INVENTION

To this end, the invention proposes a method for monitoring a visual capacity modification parameter of a user of at least one display device, the visual capacity modification parameter being indicative of the modification of a parameter linked to the visual capacity of the user related to the use of the at least one display device, the method comprises:
  a display use data determining step during which display use data indicative of a use of the at least one display device by the user are determined,
  a visual capacity modification parameter determining step during which a modification parameter of the visual capacity of the user is determined based on said display use data, and
  an information generating step during which an information based on said modification parameter of the visual capacity of the user is generated.

Advantageously, the method according to the invention helps the user/consumer of display devices manage his eyesight requirements or usage throughout the day and thus avoid visual inconvenience for example blur vision, eye dryness, headaches, mood, diplopia, strabismus, etc. Furthermore, the method may help the user avoid a possible increase in myopia over time.

A monitoring component adapted and configured to implement such a method according to the invention interacts with the consumer when he is using its intermediate and/or near vision for looking the display to avoid him experiencing symptoms as described hereinbefore.

From the determination of display use data, a modification parameter of the visual capacity of the user is determined based on said display use data, for example a risk of deterioration of the visual capacity of the user. Then, the information generated from the modification parameter can alert the consumer and a solution can be proposed to reduce this risk, for example recommending the consumer to perform eye exercises for his eyes at appropriate times.

According to further embodiments of the method which can be considered alone or in combination:
  the visual capacity modification parameter is a visual capacity deterioration risk indicative of the risk of deterioration of the visual capacity of the user related to the use of the at least one display device;
  the visual capacity modification parameter is a parameter linked to improved visual capacity of the user related to the use of the at least one display device;
  the information comprises at least a control signal configured to be sent to and to control the at least one display device and based on said visual capacity modification parameter of the user;
  the information generating step comprises a recommendation data providing step during which a recommendation data based at least on the determined visual capacity modification parameter is generated;
  the recommendation data comprises an alert indicative of the determined visual capacity modification parameter;
  the method further comprises a display device data providing step during which display device data indicative of each display device used by the user are provided, and:
    the display use data measuring step is repeated for each display device used by the user, and.
    the visual capacity modification parameter is determined based on said display device data and on each measured display use data indicative of a use of each display device by the user;
  the display use data determining step comprises a display use data sending step during which determined display use data indicative of a use of each display device by the user are sent to an information generating unit, and the information generating unit is a distant entity from at least one of the display devices and is configured to receive the display use data and the display device data from each display devices;
  the method further comprises a display use data storing step during which the determined display use data are stored over time and wherein the visual capacity modification parameter is indicative of the evolution over time of the modification parameter of the visual capacity of the user related to the use of the at least one display device;
  display use data indicative of a use of the at least one display device by the user comprise at least the time spent to watch the display device and/or the distance between the display and the user used for watching the display device and/or the gazing direction of at least one of the eyes of the user on the display and/or the type of visual activity when watching the display device and/or the relative position of the display device and the user;

the method further comprises a user identification step during which the user using the at least one display device is identified;

the visual capacity modification parameter comprises a eyestrain risk and/or a eye dryness risk and/or a red eyes risk and/or a ciliary muscle tiredness risk and/or a nearsightedness risk and/or a myopic evolution risk and/or a visual performance loss risk.

The invention also relates to a monitoring component for monitoring a visual capacity modification parameter of a user of at least one display device, the monitoring component comprising:

a memory configured to store computer executable code, and a processor configured to execute the following computer executable codes stored in the memory:

a communication code configured to received display use data indicative of a use of the at least one display device by the user sensed by at least one sensor, a visual capacity modification parameter determining code configured to determine a visual capacity modification parameter based on said display use data received from the sensor, and an information generating code configured to generate an information indicative of said modification parameter of the visual capacity of the user based at least on the determined visual capacity modification parameter.

According to further embodiments of the monitoring component which can be considered alone or in combination:

the information generating code is configured to provide a recommendation data based at least on the determined visual capacity modification parameter;

the recommendation data comprises an alert indicative of the determined visual capacity modification parameter;

the at least one sensor is configured to sense at least one feature indicative of a visual parameter of a user of the display device;

the at least one sensor is embedded in the display device;

the at least one sensor is a distant entity from the display device;

the display device comprises an identification unity configured to identify the user when the user watches the display device, the communication code is further configured to receive identification data from the identification unity, and the visual capacity modification parameter is further determined based on said identification data received from the identification unity.

Furthermore, the invention concerns a head mounted device configured to be worn by a wearer, comprising:

a display device configured to be watched by the wearer, at least one sensor configured to sense display use data indicative of a use of the at least one display device by the wearer, and a communication component configured to communicate display use data indicative of a use of the at least one display device by the wearer sensed by the at least one sensor to a monitoring component.

Another aspect of the invention relates to a display device comprising:

a display configured to be watched by a user, at least one sensor configured to sense display use data indicative of a use of the display device by the user, and a communication component configured to communicate display use data indicative of a use of the at least one display device by the wearer sensed by the at least one sensor to a monitoring component.

The invention further relates to a computer program product comprising one or more stored sequences of instructions that are accessible to a processor and which, when executed by the processor, causes the processor to carry out at least the display use data determining step, the visual capacity modification parameter determining step and the information generating step of the method according to the invention.

The invention also relates to a computer-readable storage medium having a program recorded thereon; where the program makes the computer execute at least the display use data determining step, the visual capacity modification parameter determining step and the information generating step of the method of the invention.

The invention further relates to a device comprising a processor adapted to store one or more sequence of instructions and to carry out at least the display use data determining step, the visual capacity modification parameter determining step and the information generating step of the method according to the invention.

Unless specifically stated otherwise, as apparent from the following discussions, it is appreciated that throughout the specification discussions utilizing terms such as "computing", "calculating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes presented herein are not inherently related to any particular computer or other apparatus. Various general purpose systems may be used with programs in accordance with the teachings herein, or it may prove convenient to construct a more specialized apparatus to perform the desired method.

The desired structure for a variety of these systems will appear from the description below. In addition, embodiments of the present invention are not described with reference to any particular programming language. It will be appreciated that a variety of programming languages may be used to implement the teachings of the inventions as described herein.

BRIEF DESCRIPTION OF THE DRAWINGS

Non limiting embodiments of the invention will now be described, by way of example only, and with reference to the following drawings in which.

Figure 1:
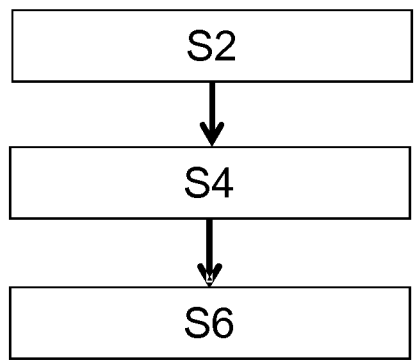
FIG. 1 is a flow chart of a method according to a first embodiment of the invention.

Various aspects are now described with reference to the drawings, wherein like reference numerals are used to refer to like elements throughout. In the following description, for purposes of explanation, numerous specific details are set forth in order to provide a more thorough understanding of one or more aspects. It is evident, however, that such aspects can be practiced without these specific details. In other instances, structures and devices are shown in block diagram form in order to facilitate describing one or more aspects.

DETAILED DESCRIPTION OF PREFERRED EMBODIMENTS

As illustrated on FIG. 1, the invention relates to a method for monitoring a visual capacity modification parameter of a user of at least one display device. In the sense of the invention, the visual capacity modification parameter is a parameter indicative of the modification of a parameter linked to the visual capacity of the user related to the use of the at least one display device.

More particularly, the visual capacity modification parameter is a visual capacity deterioration risk indicative of the risk of deterioration of the visual capacity of the user related to the use of the display devices.

According to another embodiment, the visual capacity modification parameter is a parameter linked to improved visual capacity of the user related to the use of the display devices. For example, an improved visual capacity may be a parameter showing that for a myopic child, the reading distance goes from a too short distance to a correct distance.

The method comprises at least the following steps:
a display use data determining step S2,
a visual capacity modification parameter determining step S4, and
an information generating step S6.

During the display use data determining step S2, display use data indicative of a use of the at least one display device by the user are determined.

The display use data may be determined by measuring at least one parameter linked to the vision of the user/consumer on the screen of the display device by a sensor embedded or not in the display device, for example the time spent to watch the screen, the distance used for watching the screen of the display device, the type of visual task, etc. . . . .

Another way to determine the display use data may be to ask the wearer to answer some questions like "how long do you stare at the screen of the display device without looking far away?" or other similar questions.

Advantageously, display use data indicative of a use of the at least one display device by the user comprise one or several parameters chosen among:
the time spent to watch the display device,
the distance between the display and the user used for watching the display device,
the gazing direction of at least one of the eyes of the user on the display,
the type of visual activity when watching the display device, and/or
the relative position of the display device and the user.

For example, the eye blink frequency of the user can be detected with a front camera in the case wherein a front camera is embedded in the display device and a level of tiredness can be thus determined. If this level is too high, a notification message will be displayed on the screen to alert the user.

Advantageously, the method may comprise a display use data storing step during which the determined display use data are stored over time. In such embodiment, the visual capacity modification parameter is indicative of the evolution over time of the modification parameter of the visual capacity of the user related to the use of the at least one display device.

During the visual capacity modification parameter determining step S4, a modification parameter of the visual capacity of the user is determined based on said display use data.

Preferably, the visual capacity modification parameter comprises one or several parameters chosen among:
a eyestrain risk,
a eye dryness risk,
a red eyes risk,
a ciliary muscle tiredness risk,
a nearsightedness risk,
a myopic evolution risk, and/or
a visual performance loss risk.

Furthermore, the method may comprise a reference level determining step during which a reference level may be determined. The reference level can be a standard reference level of at least a visual capacity parameter or an individualized reference level based on previous determination or measurement of at least a visual capacity parameter of the user.

Then, during the information generating step S6, an information based on said modification parameter of the visual capacity of the user is generated.

Preferably, the information comprises at least a control signal configured to be sent to the at least one display device in order to control the at least one display device. The control signal is also based on said visual capacity modification parameter of the user.

Advantageously, the information generating step S6 comprises a recommendation data providing step during which a recommendation data based at least on the determined visual capacity modification parameter is generated. The recommendation data preferably comprises an alert indicative of the determined visual capacity modification parameter.

For example, the recommendation data aims to alert the user/consumer when the risk of deterioration of the visual capacity of the user is important. Furthermore, the recommendation data can also propose to the user a solution for the modification of the visual capacity linked to the risk, if the risk is confirmed, for example by sending a visual recommendation to limit this risk or shut down the screen. A visual recommendation to limit the risk may comprise exercise to ease accommodation.

According to an advantageous embodiment, the method further comprises a display device data providing step S8 during which display device data indicative of each display device used by the user are provided, for example the type, size, brightness of the screen display of each display device.

In such embodiment, the display use data determining step S2 is repeated for each display device used by the user and the visual capacity modification parameter is determined based on said display device data and on each determined display use data indicative of a use of each display device by the user.

Preferably, the display use data determining step S2 comprises a display use data sending step during which determined display use data indicative of a use of each display device by the user are sent to an information generating unit. Furthermore, the information generating unit is a distant entity from at least one of the display devices and is configured to receive the display use data and the display device data from each display devices.

This embodiment which relates to a cloud solution is particularly interesting and advantageous. Indeed, a cross experience can be obtained between all the devices of one or several users during a predetermined period: TV, smartphone, tablet and laptop for example.

Advantageously, if different consumers usually used one or several display devices, the method may comprise a user identification step during which the user using the at least one display device is identified.

For example, the use duration of a screen is easily detected for a consumer with a cloud solution as described above. Indeed, the use duration of smartphone, tablet and laptop can be gathered and the use duration of a display device by the user can be then determined independently of the device. The consumer can be identified by its key or login on the device, or by a face recognition or a habit (time, place, habit) if the display device is adapted and configured to do it.

Figure 2:
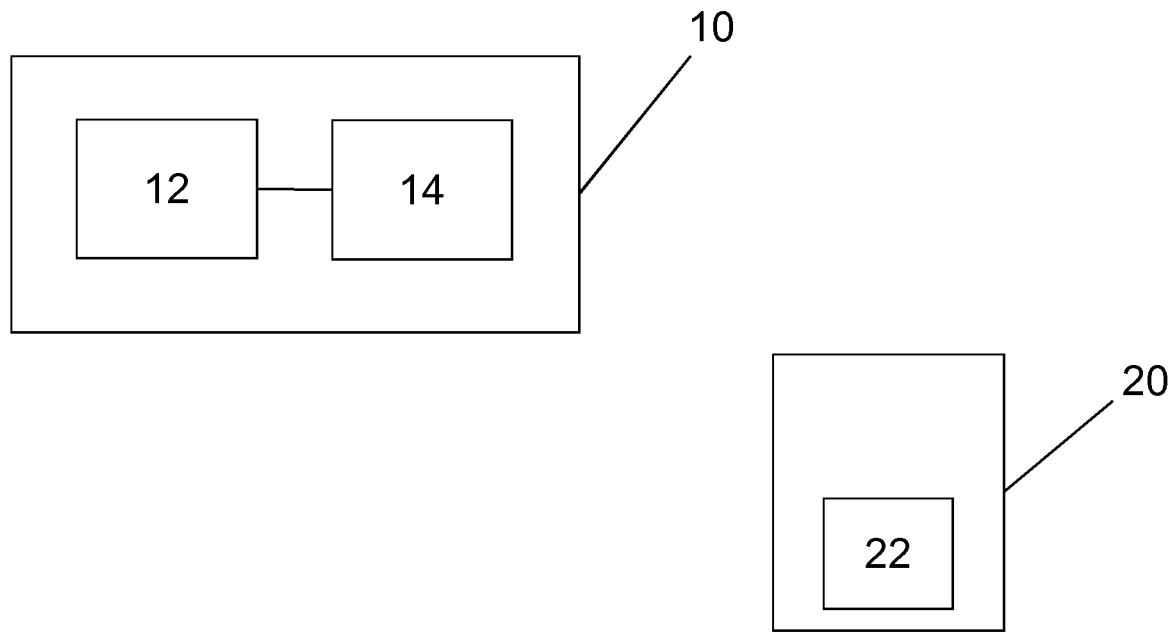
FIG. 2 is an illustration of a block diagram of an exemplary non-limiting monitoring component according to an embodiment of the invention.

The invention also relates to a monitoring component adapted and configured to implement a method according to the invention for monitoring a visual capacity modification parameter of a user of at least one display device. An embodiment of such a monitoring component is schematically illustrated on FIG. 2.

More particularly, the monitoring component 10 comprises a memory 12 configured to store computer executable codes and a processor 14.

The processor 14 is configured to execute the following computer executable codes stored in the memory 12:
  a communication code,
  a visual capacity modification parameter determining code, and
  an information generating code.

The communication code is configured to received display use data indicative of a use of the at least one display device 20 by the user sensed by at least one sensor 22.

The or each of the sensors are embedded in one of the display devices (as illustrated on FIG. 2) or in a distant unity. Furthermore, the or each sensor is configured to sense at least one feature indicative of a visual parameter of a user of the display device, for example the time spent to watch the display device, the distance between the display and the user used for watching the display device, the gazing direction of at least one of the eyes of the user on the display, the type of visual activity when watching the display device, and/or the relative position of the display device and the user.

The visual capacity modification parameter determining code is configured to determine a visual capacity modification parameter based on said display use data received from the sensor.

The information generating code is configured to generate an information indicative of said modification parameter of the visual capacity of the user based at least on the determined visual capacity modification parameter. The information generating code is preferably configured to provide a recommendation data based at least on the determined visual capacity modification parameter.

Furthermore, the recommendation data can advantageously comprise an alert indicative of the determined visual capacity modification parameter.

According to an advantageous embodiment, the display device comprises an identification unity configured to identify the user when the user watches the display device. In such an embodiment the communication code is further configured to receive identification data from the identification unity and the visual capacity modification parameter is further determined based on said identification data received from the identification unity The invention also relates to a head mounted device configured to be worn by a wearer comprising a display device configured to be watched by the wearer and adapted and configured to implement a method according to the invention for monitoring a visual capacity modification parameter of a user of at least one display device.

To this end, the head mounted device comprises advantageously at least one sensor configured to sense display use data indicative of a use of the at least one display device by the wearer and a communication component configured to communicate display use data indicative of a use of the at least one display device by the wearer sensed by the at least one sensor to a monitoring component as described hereinbefore.

Another object of the invention is a display device comprising a display configured to be watched by a user and at least one sensor configured to sense display use data indicative of a use of the display device by the user.

Furthermore, the display device comprises a communication component configured to communicate display use data indicative of a use of the at least one display device by the wearer sensed by the at least one sensor to a monitoring component.

Examples of a method and/or a device according to the invention for monitoring a visual capacity modification parameter of a user of at least one display device will now be detailed for particular applications.

In order to simplify the description, only one display device is considered, but of course the description can be easily adapted to multiple display devices.

First Example to Protect the Eyes from Digital Display Devices

In this example, the display use data indicative of a use of a display device by the user is the use duration of the screen of the display device, which can be measured by a clock of the display device during the display use data determining step S2.

For example, a time counter can be activated each time the display device is switched on to determine the time spent watching at the display device continuously. The time counter is stopped when the display device is switched off.

In another example, the display use data may be determined more finely by using information coming from an inclinometer or an accelerometer, or from a front camera of the display device to activate/deactivate the time counter. Indeed, to determine the time spent by the customer watching the display device continuously, it may be used a face detection and/or eye tracking using the front camera and software embedded in the display device to check if the user is really watching the screen of the display device. Of course, the software is a computer program product comprising one or more stored sequences of instructions that are accessible to a processor and which, when executed by the processor, causes the processor to carry out a method, here an eye tracking method or a face detection method.

The eye tracking software allows determining the gazing direction of the user, and the time counter starts when the gazing direction is toward the screen of the display device and stops when the gazing is in another direction.

In the case of a face detection software, this one allows for determining the head inclination of the user, and thus the time counter starts when the head is inclined in the direction of the screen of the display device and stops when the head inclination is different, for example straight.

The time counter may be reset when the user stops watching the screen of the display device or see in another direction during a minimum period. For example, the time counter may reset when the user looks in another direction at least 20 seconds, (i.e. if the display device is off more than 20 seconds, or if the gaze direction of the user is not toward the display for more than 20 s).

The inclinometer may also be used to determine if the user looks toward the display device or not, in addition to the switch on/off status of the display device. Indeed, if the inclination of the display device corresponds to a standard orientation (45°±20°) relative to a vertical direction), the display device is supposed to be watched by the user, whereas if the orientation differs (more particularly if the inclination is substantially equal to 0° or 90°), the display is supposed not to be watched by the user.

During the visual capacity modification parameter determining step S4, a visual capacity deterioration risk is determined based on the duration of screen use, for example a risk linked to eyestrain, eye dryness, red eyes, ciliary muscles tiredness is determined.

For example, one can consider that if the time counter shows that continuous watching the display device is:
  below 20 min: no risk of deterioration of the visual capacity of the user exists;
  more than 20 min: a risk of deterioration of the visual capacity of the user is considered to exist; and
  very important, for example more than 40 min: the risk of deterioration of the visual capacity of the user is considered to be important.

Moreover, if the time spent watching continuously the display device during many periods of the same day is more than 20 min, one can consider that the level of risk of deterioration of the visual capacity of the user increases.

Furthermore, the risk may be weighted according to the kind of images displayed. Indeed, when reading, in particular small characters, the risk of deterioration of the visual capacity of the user should increase.

During the information generating step S6, a notification message is generated and displayed on the screen of the display device to alert the user if the risk is considered to exist. It is then possible to recommend to the user to take a break and have a far vision moment or to do an accommodation relaxing exercise like the 20/20/20 exercise from Vision Council: "every 20 minutes, take a 20 second break, and stare at something 20 feet away". The front side camera can be used to check that the exercise is well executed.

Second Example to Protect the Eyes During a Long Period of Near Vision

In this example, the display use data is the distance between the screen of the display device and the eyes of the user, which can be determined by a front camera of the display device during the display use data determining step S2.

Indeed, the analysis of the picture taken by the camera with image processing tools allows determining the distance for example every minute. The simplest formula to estimate distance between the screen and the eyes is pinhole projection formula: $x/f=X/d$, wherein x is the size of the eye or the pupillary distance on the sensor, f is focal length of the lens, X is the real size of the eye or real pupillary distance, and d is distance from nodal point to the eye.

During the visual capacity modification parameter determining step S4, a visual capacity deterioration risk is determined based on the duration of the time spent in near vision, i.e. when the distance between eyes and the screen is less than the Harmon distance, for example a risk linked to the nearsightedness, the myopic evolution and eyestrain is determined.

For example, when the user is watching the display device most of the time at a distance greater than the Harmon distance, the risk is considered not to exist.

When the user frequently watches the display at a distance smaller than the Harmon distance, the risk exists.

Of course, the risk increases with shorter distance and longer duration and the risk is higher according to the age of the user.

During the information generating step S6, a notification message is generated and displayed on the screen of the display device to alert the user if the risk is considered to exist. Furthermore, a recommendation message is generated and displayed on the screen of the display device for example:
  to increase the reading distance up to the Harmon distance,
  to switch the near vision activity to a far vision activity,
  to propose a visual exercise like the 20/20/20 exercise described in the first example, and/or
  and particularly if the user is a child to switch off the display device or to blur the screen so that the distance is too small in order to avoid an increasing of the myopia progression.

Third Example to Check the Suitable Usage of a Progressive Lens (PAL)

In this third example, the display device is an eyewear or a head mounted display device comprising at least a progressive lens arranged in front of an eye of the wearer. The display use data is the position of the pupil of the eye on the lens, which can be determined by a front camera of the display device during the display use data determining step S2.

Indeed, the analysis of the picture taken by the camera with image processing tools allows determining the position of the pupil in the lens coordinate system for example every minute. For example, the pixel distance between the eye center and a reference on the frame be counted to determine the position eye in the lens on the picture. The distance between the eye/pupil center and the reference on the frame can be determined:
  horizontally, to check that the wearer is using a part of the lens close to the meridian line when watching the display device. Indeed, if the horizontal distance is too high, the wearer will experiment blur, because the gaze direction may be out of the field of view provided by the lens, vertically: if the customer does not correctly use the near or intermediate vision area provided by the lens, he may experiment blur or induce supplementary accommodation to get a sharp vision. For example, a child wearing progressive lens should have his gaze direction going through the near vision area of the lens so as to be efficient.

The gaze direction is determined from the camera and an eye tracking software and the position of the pupil in the lens can be determined using for example image processing to detect the edges of the frame or of the lens.

The position of the meridian line and the near/far visions in the right/left lenses may be determined from user individual data coming from the optician. As an alternative, if these data are not provided, it is possible to consider standard meridian line position, standard near/far vision position.

During the visual capacity modification parameter determining step S4, a visual capacity deterioration risk is determined, for example a risk linked to the visual comfort and performance is determined. More precisely, if the wearer does not use correctly the PAL lens, he will experiment blur and fatigue. For children wearing PAL lens for myopia control, the risk is that myopia progresses despite the use of PAL lenses.

The risk is determined based on the shift of the position of the pupil compared to a theoretical position:
  the risk is considered low if the gaze direction is within the field of view and the difference between the distance between the wearer and the display device and the normal distance provided by the lens area that intersect the gazing direction is under 1D. For example, if the distance between the wearer and the display is about 40 cm (i.e. about 2.5 D) and the wearer is looking through an area of the lens usually configured to provide power for object at 60 cm (i.e. intermediate vision), this means that the wearer will have an extra accommodation of 1/0.4−1/0.6=0.83 Diopters which is acceptable.
  it can be considered that the risk is important if the gaze direction is outside the field of vision, frequently or most of the time and/or if the near vision area of the lens is not used whereas the wearer is watching the display at near distance.

During the information generating step S6, if the pupil center is not well positioned in near vision zone of the lens, a recommendation message is generated and sent to the user to recommend him to stand up the head to use better the near vision zone in the lens or to put the eyewear back on the nose. It is also possible to recommend the wearer to change his head posture so that horizontal shift is reduced.

Fourth Example to Deal with Glide of the Eyewear on the Nose of the Wearer

In this fourth example, the display device is an eyewear or a head mounted display device comprising a frame and at least an ophthalmic lens arranged in front of an eye of the wearer, preferably a progressive lens. The display use data is the position of the frame of the eyewear on the user face, which can be determined by a front camera of the display device during the display use data determining step S2.

Indeed, the analysis of the picture taken by the camera with image processing tools allows determining the position of the frame in the face coordinate system for example every minute.

During the visual capacity modification parameter determining step S4, a visual capacity deterioration risk is determined, for example a risk linked to the visual comfort and performance is determined. The risk is determined based on the shift of the position of the frame compared to an initial position.

The shift of the frame will impact the way the lens is used and so the visual performance of the wearer:
  if the area of the progressive lens is not used correctly for near/intermediate vision as described in the third example;
  the posture of the head of the wearer may be uncomfortable so as to use correctly the area of the progressive lens, leading to pains in the back or neck;
  for progressive lenses, when the wearer go back to far vision, he may have a reduced field of vision because the far vision area of the lens is shifted down.

During the information generating step S6, a recommendation is sent to the user to put the eyewear back on the nose if the frame is not well positioned. Another recommendation may be to go the optician to adjust the frame.

The invention has been described above with the aid of embodiments without limitation of the general inventive concept.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A method for monitoring a visual capacity modification parameter of a user of a plurality of display devices, the visual capacity modification parameter being indicative of modification of a parameter linked to a visual capacity of the user related to a use of the plurality of display devices, the method comprising:
  determining display use data indicative of a use of each display of the plurality of display devices by the user;
  determining a modification parameter of the visual capacity of the user based on said display use data; and
  generating information based on said modification parameter of the visual capacity of the user.

2. The method according to claim 1, wherein the visual capacity modification parameter is a visual capacity deterioration risk indicative of a risk of deterioration of the visual capacity of the user related to the use of the plurality of display devices.

3. The method according to claim 1, wherein the visual capacity modification parameter is a parameter linked to improved visual capacity of the user related to the use of the plurality of display devices.

4. The method according to claim 1, wherein the information comprises at least a control signal configured to be sent to and to control each of the plurality of display devices and is based on said visual capacity modification parameter of the user.

5. The method according to claim 1, wherein the generating further comprises generating recommendation data based at least on the determined visual capacity modification parameter.

6. The method according to claim 5, wherein the recommendation data comprises an alert indicative of the determined visual capacity modification parameter.

7. The method according to claim 1, further comprising
obtaining display device data indicative of each display device of the plurality of the display devices used by the user,
wherein:
the visual capacity modification parameter is determined based on said display device data and on each determined display use data indicative of a use of each display device by the user.

8. The method according to claim 7, wherein the determining the display use data further comprises sending determined display use data, indicative of a use of each display device by the user, to an information generating unit, and
the information generating unit is a distant entity from at least one of the display devices and is configured to receive the display use data and the display device data from each display device of the plurality of display devices.

9. The method according to claim 1, further comprising storing the determined display use data over time,
wherein the visual capacity modification parameter is indicative of an evolution over time of the modification parameter of the visual capacity of the user related to the use of the plurality of display devices.

10. The method according to claim 1, wherein display use data indicative of a use of the plurality of display devices by the user includes at least time spent to watch each display device and/or a distance between the display and the user used for watching the display device and/or a gazing direction of at least one of eyes of the user on each display and/or a type of visual activity when watching each display device and/or a relative position of each display device and the user.

11. The method according to claim 1, further comprising identifying the user using each of the plurality of display devices.

12. The method according to claim 1, wherein the visual capacity modification parameter comprises an eyestrain risk and/or an eye dryness risk and/or a red eyes risk and/or a ciliary muscle tiredness risk and/or a nearsightedness risk and/or a myopic evolution risk and/or a visual performance loss risk.

13. A monitoring apparatus for monitoring a visual capacity modification parameter of a user of a plurality of display devices, the monitoring apparatus comprising:
a memory configured to store computer executable code; and
a processor that when executing the computer executable code stored in the memory, is configured to:
receive display use data indicative of a use of each of the plurality of display devices by the user sensed by at least one sensor,
determine a visual capacity modification parameter based on said display use data received from the at least one sensor, and
generate information indicative of said modification parameter of the visual capacity of the user based at least on the determined visual capacity modification parameter.

* * * * *